United States Patent
Harding et al.

(10) Patent No.: US 11,134,957 B2
(45) Date of Patent: Oct. 5, 2021

(54) TRANSRADIAL SHEATH SUPPORT AND HEMOSTASIS DEVICE AND METHOD

(71) Applicants: Jonathan Cole Harding, Littleton, CO (US); Philip Harding, Littleton, CO (US); William L. Schaal, Denver, CO (US)

(72) Inventors: Jonathan Cole Harding, Littleton, CO (US); Philip Harding, Littleton, CO (US); William L. Schaal, Denver, CO (US)

(73) Assignee: STAT BAND, LLC, Denver, CO (US)

( * ) Notice: Subject to any disclaimer, the term of this patent is extended or adjusted under 35 U.S.C. 154(b) by 534 days.

(21) Appl. No.: 15/694,525

(22) Filed: Sep. 1, 2017

(65) Prior Publication Data
US 2019/0069904 A1    Mar. 7, 2019

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1325* (2013.01); *A61B 17/1355* (2013.01);
(Continued)

(58) Field of Classification Search
CPC ...... A61M 2025/024; A61M 2025/026; A61M 2025/0253; A61M 2025/0246;
(Continued)

(56) References Cited

U.S. PATENT DOCUMENTS 2,402,306 A * 6/1946 Turkel ............... A61M 5/32
                                                  604/174
2,660,174 A * 11/1953 Saemann ............ A61B 5/0235
                                                  606/202
(Continued)

FOREIGN PATENT DOCUMENTS

WO    2016095038 A1    6/2016

OTHER PUBLICATIONS

International Search Report and Written Opinion dated Jan. 2, 2019 in International Application No. PCT/US18/48899.

*Primary Examiner* — Nathan R Price
*Assistant Examiner* — Mark A Igel
(74) *Attorney, Agent, or Firm* — Berg Hill Greenleaf Ruscitti, LLP (57) ABSTRACT

The invention includes a transradial introducer sheath support and integral hemostasis device. The device includes a wristband and an introducer sheath support mount attached to the wristband. The wristband is made from a flexible and resilient material that is applied to the distal forearm of the patient or other desired location on the patient. The support mount may be a molded unitary structure, such as made from a thermoplastic material, and is attached directly to the outer surface of the wristband. An inflatable hemostatic element is incorporated in the wristband and mounted to an interior surface of the wristband. The hemostatic element may be selectively inflated to apply pressure to a radial access point of the patient during and after removal of the transradial introducer sheath from the patient. Another embodiment provides a hemostatic element by a rotatable clasp of the sheath support mount.

23 Claims, 9 Drawing Sheets

(51) Int. Cl.
*A61M 25/02* (2006.01)
*A61M 5/158* (2006.01)
*A61B 17/00* (2006.01)
*A61B 17/12* (2006.01)
*A61B 90/00* (2016.01)

(52) U.S. Cl.
CPC ..... *A61M 25/02* (2013.01); *A61B 2017/00557* (2013.01); *A61B 2017/00862* (2013.01); *A61B 2017/12004* (2013.01); *A61B 2090/065* (2016.02); *A61M 2005/1586* (2013.01); *A61M 2025/0206* (2013.01); *A61M 2210/083* (2013.01)

(58) Field of Classification Search
CPC .. A61M 2025/0213; A61M 2025/0206; A61M 2025/028; A61M 2025/0293; A61M 39/06; A61M 2005/1586; A61M 2210/083; A61B 17/0057; A61B 17/132; A61B 17/1322; A61B 17/135; A61B 17/1325; A61B 17/1355; A61B 17/0469; A61B 17/12004; A61B 17/12022; A61B 25/02; A61B 25/0662; A61B 2090/065; A61B 2017/00557; A61B 2017/00862; A61B 2017/12004; A61F 2/966
See application file for complete search history.

(56) References Cited

U.S. PATENT DOCUMENTS

| | | | | |
|---|---|---|---|---|
| 3,059,645 | A * | 10/1962 | Hasbrouck | A61M 25/02 604/179 |
| 3,120,846 | A * | 2/1964 | Fletcher | A61B 17/135 606/202 |
| 3,630,195 | A * | 12/1971 | Santomieri | A61M 25/02 604/180 |
| 3,765,421 | A * | 10/1973 | Poprik | A61M 25/02 604/179 |
| 4,096,863 | A * | 6/1978 | Kaplan | A61M 25/02 128/DIG. 26 |
| 4,316,461 | A * | 2/1982 | Marais | A61M 25/02 128/DIG. 26 |
| 4,470,410 | A * | 9/1984 | Elliott | A61B 5/52 128/877 |
| 4,574,798 | A * | 3/1986 | Heitzman | A61M 25/02 128/205.22 |
| 4,591,356 | A * | 5/1986 | Christie | A61M 25/02 128/DIG. 26 |
| 4,896,465 | A * | 1/1990 | Rhodes | A61M 5/1418 128/849 |
| 5,037,398 | A * | 8/1991 | Buchanan | A61M 25/02 604/180 |
| 5,190,530 | A * | 3/1993 | Greeff | A61M 25/02 604/179 |
| 5,496,282 | A * | 3/1996 | Militzer | A61M 25/02 604/179 |
| 5,577,516 | A * | 11/1996 | Schaeffer | A61F 5/05866 128/858 |
| 5,578,013 | A * | 11/1996 | Bierman | A61M 25/02 128/DIG. 26 |
| 5,941,856 | A * | 8/1999 | Kovacs | A61M 25/02 604/179 |
| 7,879,013 | B2 * | 2/2011 | Smith | A61M 25/02 604/174 |
| 8,777,982 | B2 * | 7/2014 | Clark | A61B 17/0057 606/201 |
| 9,463,026 | B2 * | 10/2016 | Corrigan, Jr. | A61B 17/1325 |
| 2002/0156423 | A1 * | 10/2002 | Tollini | A61M 25/02 604/180 |
| 2005/0125025 | A1 | 6/2005 | Rioux | |
| 2008/0132848 | A1 * | 6/2008 | Wright | A61M 25/013 604/174 |
| 2009/0281565 | A1 * | 11/2009 | McNeese | A61B 17/1327 606/201 |
| 2012/0143140 | A1 * | 6/2012 | Bierman | A61M 25/02 604/174 |
| 2012/0296369 | A1 * | 11/2012 | Atthoff | A61B 17/1322 606/202 |
| 2013/0023734 | A1 * | 1/2013 | Okamura | A61B 17/1325 600/227 |
| 2013/0218073 | A1 * | 8/2013 | Ekdahl | A61M 1/3661 604/67 |
| 2013/0237866 | A1 * | 9/2013 | Cohen | A61B 5/445 600/502 |
| 2014/0012313 | A1 * | 1/2014 | Finkielsztein | A61B 17/135 606/202 |
| 2014/0018845 | A1 | 1/2014 | Lampropoulos et al. | |
| 2015/0018869 | A1 * | 1/2015 | Benz | A61B 17/135 606/203 |
| 2015/0201948 | A1 * | 7/2015 | Kornowski | A61B 17/1325 606/203 |
| 2015/0327870 | A1 * | 11/2015 | Fortson | A61B 17/0057 606/202 |
| 2015/0342615 | A1 * | 12/2015 | Keinan | A61B 17/1322 604/179 |
| 2016/0106958 | A1 * | 4/2016 | Price | A61M 25/02 604/179 |
| 2016/0174952 | A1 * | 6/2016 | Shah | A61B 17/1325 606/213 |
| 2017/0136215 | A1 * | 5/2017 | Harders | A61M 25/02 |
| 2017/0150972 | A1 | 6/2017 | Kruk | |
| 2018/0070956 | A1 * | 3/2018 | Lampropoulos | A61B 17/135 |
| 2018/0177982 | A1 * | 6/2018 | Albany | A61B 5/021 |
| 2019/0015636 | A1 * | 1/2019 | Robinson | A61M 25/02 |
| 2019/0150938 | A1 * | 5/2019 | Hazama | A61B 17/135 |

\* cited by examiner

TRANSRADIAL SHEATH SUPPORT AND HEMOSTASIS DEVICE AND METHOD

FIELD OF THE INVENTION

The invention relates to a device for supporting a transradial sheath, and more particularly, a device and method with combined functionality for supporting the sheath and providing hemostasis.

BACKGROUND OF THE INVENTION

Transradial catheterization is an endovascular procedure performed to diagnose and treat endovascular diseases. A medical practitioner has options for achieving access into the patient's arterial system in order to conduct the procedure. Traditionally, femoral arterial access was the most common approach to perform cardiac catheterization decrease for more invasive cardiology. However more recently, brachial arterial or radial arterial access has become more popular because of various advances with miniaturized catheters in which hemostasis complications can be reduced. There are a vast array of diseases that may be diagnosed and treated by a catheterization procedure, including coronary artery disease, peripheral artery disease, and others.

With transfemoral access, bleeding complications are typically higher than transradial access. Another potential drawback with transfemoral catheterization is the increased rate of hematomas which can develop after the procedure. With various advances in sheath and catheter designs for transradial catheter devices, radial artery access is becoming the preferred method of access to treat even the more complex coronary artery diseases.

Other advantages of transradial access include a shorter time for post-procedure immobilization and generally a more comfortable procedure for many patients that may have chronic back pain or other conditions which make femoral access more difficult. Additionally, transradial catheterization devices can be made smaller than transfemoral catheterization devices and therefore, there is certain cost advantages associated with both a shortened post procedure and less costly hemostasis devices While transradial catheterization and subsequent hemostasis devices have proven to be effective and a minimally invasive technique to perform endovascular procedures, there are still some disadvantages associated with these two distinct or separate steps in completing endovascular procedures.

The actual transradial catheterization procedure first requires a transradial sheath support device to be secured to the patient. In one form, the sheath support device may be an adhesive patch with a sheath support structure which is mounted to the adhesive patch. One example of a commercially available sheath support device includes Tegarderm® manufactured by 3M®. This device includes a flexible adhesive patch that is applied to the rest of the patient and a sheath support mount on the exterior surface of the patch allows the radial catheter to be mounted. Once the procedure has been conducted, the sheath support must be removed and hemostasis is conducted to stop bleeding. Radial artery compression is then conducted in which a hemostatic device is located over the access point and pressure is selectively applied over a period of time to stop the bleeding. In one form, the hemostatic device may include a wristband that is secured to the patient in which the device is either tightened or inflated to apply direct pressure at the access site. Because the sheath support must be first removed prior to applying the compression device, the catheter and other connected components must be manually held until the compression device is in place so that the introducer sheath of the catheter may then be removed.

While the use of separate sheath support and hemostatic devices can be used to conduct an effective medical procedure, there is a need for a combined sheath support and hemostatic device that may further simplify the procedure as well as to reduce costs by the provision of a single multi-functional device.

SUMMARY OF THE INVENTION

The invention in one embodiment is a transradial introducer sheath support and hemostasis device. The transradial introducer sheath support is especially adapted for use in a medical procedure involving radial artery access. The structure of the invention includes a wristband and an introducer sheath support mount that is attached to the wristband. The wristband is made from a flexible and resilient material that is applied to the distal forearm of the patient. The wristband can be adjusted to fit the patient with a closure device that also locks or holds the wristband in place. The support mount may be a unitary structure, such as one that may be molded from a thermoplastic material, and is attached directly to the outer surface of the wristband.

Also in accordance with the first embodiment, a hemostatic element is incorporated in the wristband in which this hemostatic element is mounted to an interior surface of the wristband and aligned with the support mount. According to one aspect of this embodiment, the hemostatic element may take the form of an inflatable member which is selectively inflated to apply pressure to the radial access point after removal of the transradial introducer sheath.

According to another aspect of this first embodiment, the support mount may include a base portion and a clasp which allows a user to selectively secure and remove a transradial introducer sheath used in the medical procedure. The clasp includes a pair of side rails positioned on opposite lateral sides of the base portion and a bridge which interconnects respective distal ends of the side rails. Proximal ends of the side rails are integral with an integral hinge that is formed by thinned sections of material adjacent the proximal ends.

In use, the clasp is opened and a transradial introducer sheath is placed on the support mount. The clasp is then closed to capture and hold the sheath. A large opening in the front portion of the support mount allows the transradial sheath to extend forward. A lateral portion of the introducer sheath is captured in at least one lateral opening of the support mount formed by a gap between the corresponding side rail and base portion of the support mount. In this configuration, the support amount enables the introducer sheath to be effectively held by the clasp and also to accommodate one or more lateral side ports or side branches which may be present in the particular design of the introducer sheath.

According to another preferred embodiment of the device of the invention, a different configuration is provided for the clasp in which the clasp is rotatable between a first position to lock and hold a surgical device such as an introducer sheath, and a second position in which the clasp serves as a hemostasis element to apply pressure to the access point where the introducer needle was emplaced in a patient. In the first position, the clasp is oriented such that it presents an upper curved convex surface thereby creating a gap between a lower surface of the clasp cover and an exterior surface of the wristband. In the second position, the clasp is rotated so that the convex surface is reversed and is placed in contact with the access point to apply selective hemostatic pressure. The convex shape provides a centrally aligned, continuous and uniform curvature that allows the clasp to contact any number of points on a linear orientation that may require hemostasis. Therefore when aligning the device for use, so long as the clasp when rotated to the second position is correctly aligned laterally across the patient's wrist or arm, the length of the clasp in a longitudinal direction, will be adequate to contact the access point where the sheath was removed from the patient.

According to another aspect of the invention, a method is provided for transradial arterial access and subsequent hemostatic pressure within a single device. A user selects an introducer sheath and makes arterial access according to the medical procedure. The body of the introducer sheath is secured to the support mount. The wristband is placed over the distal forearm/wrist area of the patient and the hemostatic element is centered over the arterial access point. The wristband is sufficiently tightened to prevent inadvertent movement or shifting of the introducer sheath; however, the hemostatic element is not inflated to apply pressure. When the medical procedure is completed, the introducer sheath is removed from the patient's artery. At a desired time during and after or after removal of the sheath, the hemostatic element is inflated to a desired pressure. This desired time could be nearly simultaneous with the removal of the sheath so that immediate pressure is applied to the arterial access point after sheath removal.

According to another aspect of this method, just prior to removal of the sheath, the hemostatic element may be slightly pressurized such that the attending medical person may remove the introducer sheath from the artery but some amount of pressure is already applied upon removal of the sheath. The hemostatic element may be selectively inflated to apply additional pressure.

According to another aspect of the method, the specific location, size, and shape of the hemostatic element may be preselected or preconfigured to best accommodate the patient and/or procedure. For example, the hemostatic element may be selectively located to most effectively provide pressure on the artery access location in which the element is secured to the wristband at that location. The size and shape of the hemostatic element may include shapes such as round, oval, rectangular, and others. The size of the hemostatic element can be varied to provide a desired area of compression surrounding the access point.

According to another aspect of the invention, the amount of force transferred to the access point can also be selectively varied by not only adjusting the amount the hemostatic element is inflated, but also by the stiffness or resiliency of the material used for the hemostatic element. For example, considering the same level or degree of inflation for the hemostatic element, material that is thicker and less flexible may allow a greater amount of pressure to be applied directly on the access point while material that is thinner and more flexible may allow a lesser amount of pressure to be applied on the access point.

According to another aspect of the invention, the wristband itself may be an inflatable member in which the wristband is selectively inflated to ensure the mounted introducer sheath remains stable on the patient. After the introducer sheath is removed, the level at which the wristband is inflated along with the level at which the hemostatic element is inflated can be considered in determining an optimal range of pressures to be applied to the access point for conducting hemostasis.

According to another aspect of the invention, the hemostatic element may be coated with a sterile therapeutic coating to assist in maintaining sterility and thus an efficient hemostasis effort in which separate steps are not required to keep the access point clean or sterile.

There are a number of advantages to the device and method of the invention. One clear advantage over the prior art is that a single device is provided for both stabilizing an introducer sheath or catheter type device and for conducting hemostasis after a medical procedure is completed. The multipurpose device therefore simplifies the procedure, minimizes the devices involved, and allows for nearly instantaneous pressure to be applied to the access point. The wristband provides a relatively large but unobtrusive structure for securing the support mount. The hemostatic element is already in place such that there are no extra steps of manipulating equipment or application of intermediate pressure by another device prior to activation of the hemostatic element.

Considering the above features of the invention, in one aspect, it may be considered a transradial sheath support and hemostasis device comprising: a flexible wristband; a closure device incorporated on the wristband to selectively size a circumference of the wristband with respect to a patient who receives the wristband; a sheath support mounted to the wristband, said sheath support comprising a base, a plurality of posts extending from the base, and a clasp rotatably connected to said supports, said sheath support being selectively movable between a first open position in which the clasp is rotated away from the base, and the closed position in which the clasp is rotated towards the base and secured thereto; and an inflatable hemostatic element secured to an interior surface of the wristband, said hemostatic element communicating with a source of air to selectively inflate said hemostatic element.

According to additional aspects of this first aspect of the invention, it may further include: wherein said clasp of said sheath support comprises a pair of spaced rails having first ends connected to corresponding posts of said plurality of posts and second ends connected to a bridge extending transversely between said rails; wherein a first opening is formed between said bridge and a front edge of said base; wherein: a pair of lateral side openings are formed between respective side rails and lateral side edges of said base; further including an inflation port communicating with said hemostatic element for introduction of air into said hemostatic element to selectively pressure said hemostatic element; further including a closure stiffener incorporated on said wristband to provide stiffening support to said closure device; and wherein said side rails each further include an engaging tips which is selectively engageable with corresponding locking flanges formed on two posts of said plurality of posts.

According to another aspect of the invention, it may be considered a transradial sheath support and hemostasis device comprising: a flexible wristband; a closure device incorporated on the wristband to selectively size a circumference of the wristband with respect to a patient who receives the wristband; a sheath support mounted to the wristband, said sheath support comprising a base, a plurality of posts extending from the base, and a clasp rotatably connected to said supports, said sheath support being selectively movable between a first open position in which the clasp is rotated away from the base, and the closed position in which the clasp is rotated towards the base and secured thereto; and means for providing hemostasis to an access point of the patient, said means for providing being secured to an interior surface of the wristband, said means for providing communicating with a source of air to selectively inflate said means for providing.

According to yet another aspect of the invention, it may be considered a method of providing transradial sheath support and hemostasis comprising: providing a flexible wristband, a closure device incorporated on the wristband to selectively size a circumference of the wristband with respect to a patient who receives the wristband, a sheath support mounted to the wristband, said sheath support comprising a base, a plurality of posts extending from the base, and a clasp rotatably connected to said supports, said sheath support being selectively movable between a first open position in which the clasp is rotated away from the base, and the closed position in which the clasp is rotated towards the base and secured thereto; providing a inflatable hemostatic element secured to an interior surface of the wristband, said hemostatic element communicating with a source of air to selectively inflate said hemostatic element; placing the wristband on a patient and aligning the hemostatic element over an access point on the patient in which access was made to a vascular system of the patient by an introducer sheath; mounting the introducer sheath on the sheath support; and selectively applying pressure to the access point at a selected time during, after, or during and after said introducer sheath is removed from the access point.

According to yet another aspect of the invention, it may be considered a transradial sheath support and hemostasis device comprising: a flexible wristband; a closure device incorporated on the wristband to selectively size the wristband with respect to a patient who receives the wristband; a transradial sheath support mounted to the wristband and a clasp rotatably connected to said sheath support, said clasp being selectively movable between a first position in which the clasp is rotated towards and secured to the wristband for securing a device such as a transradial sheath, and a second position in which the clasp is rotated away from the wristband and positioned against the patient to function as a hemostatic element by applying pressure to a selected location on the patient.

Other features and advantages of the invention will become apparent from a review of the following drawings taken in conjunction with the detailed description.

DETAILED DESCRIPTION

Figure 1:
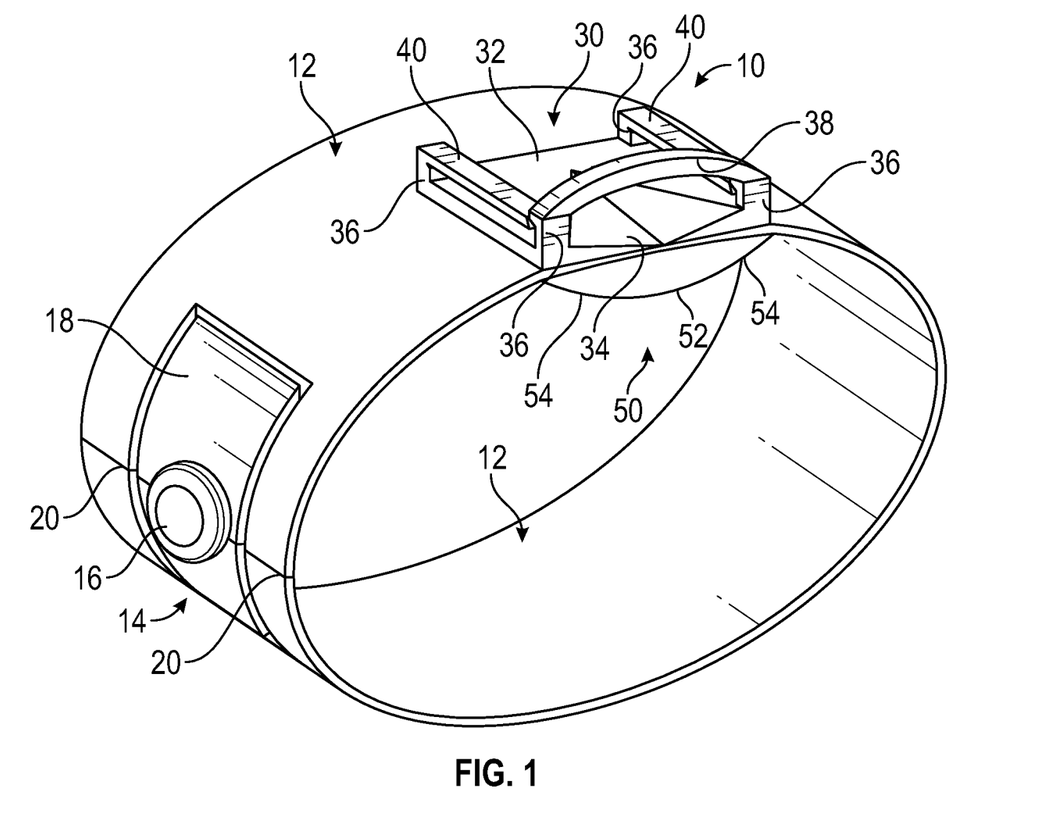
FIG. 1 is a perspective view of the device of the invention in a preferred embodiment.

Referring to FIG. 1, a first embodiment of the invention is illustrated as a transradial introducer sheath support and hemostasis device 10. The device 10 performs two primary functions, namely, as a structural support to securely mount a transradial introducer sheath and a hemostatic device to prevent continued bleeding of an access point made in the vascular system of a patient. The terms "introducer sheath" or "sheath" is intended to broadly describe any type of medical device used to access the vascular system such as a radial artery. The specific introducer sheath described and illustrated herein should therefore be interpreted as only one example of a medical device that can be supported by the device 10 of the invention. Similarly, the hemostatic function of the invention is not limited to providing hemostasis for any specific invasive medical device and rather, provides a hemostatic function for a wide range of such medical devices that make access to the vascular system.

The structure of the first embodiment is generally characterized as a wristband 12 that can be selectively sized for a patient, a support mount 30 integral with the wristband and located on an outer or exterior surface of the wristband 10, and a hemostatic element 50 secured to an interior surface of the wristband.

The wristband 12 is preferably made from a flexible material that is easily worn by a patient without chafing or other skin discomforts. The particular width and length of the wristband may be sized for any patient such that the wristband remains securely attached to the patient during the medical procedure and during the post operative time in which the hemostasis takes place.

According to one aspect of the first embodiment, the circumference of the wristband may be conveniently adjusted by use of a closure device 14. In this preferred embodiment, the closure device 14 is intended to represent a closure device such as a Boa® system that comprises a micro-adjustable dial, lightweight laces, and low friction lace guides. For simplicity in the figures, the laces and lace guides are not shown. However, it should be understood that the lace guides may be mounted to the respective facing edges of the wristband in which the laces are routed through the lace guides. As shown, the closure device 14 includes an adjustable dial or tab 16 that allows the user to selectively tighten or loosen the wristband around the patient's wrist. Accordingly, the joint or separating line 20 between the facing edges of the wristband are drawn toward one another or separated from one another in order to tighten or loosen the wristband. A relatively stiffer or thicker material 18 may surround the adjustable dial 16 to provide a more reliable means to open and close the wristband.

Figure 2:
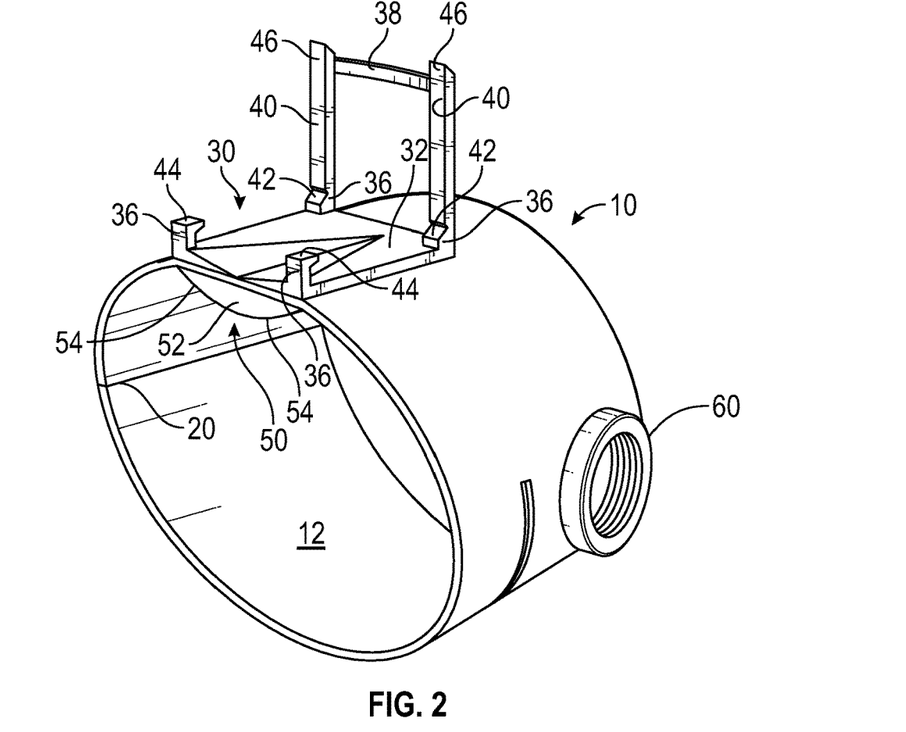
FIG. 2 is another perspective view of the device with a clasp of the invention shown in an open position.
Figure 3:
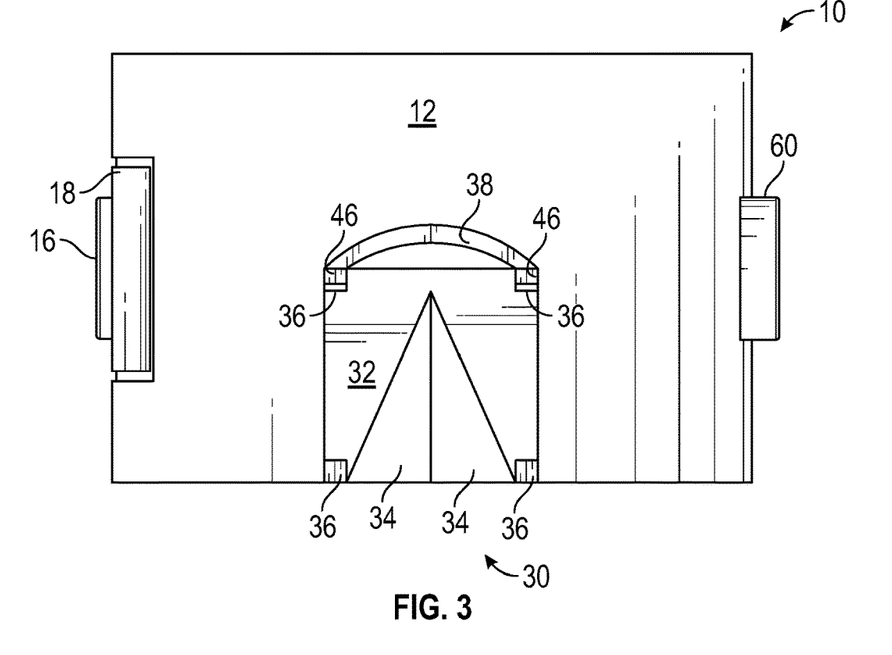
FIG. 3 is a top plan view of the device with the clasp shown in the open position.
Figure 4:
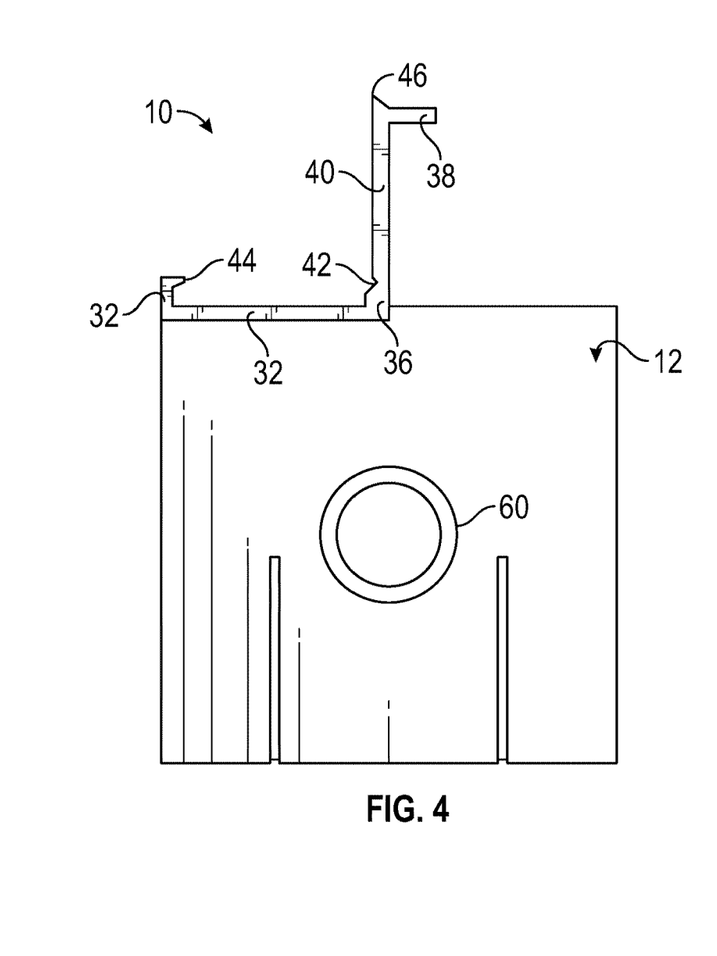
FIG. 4 is a left side elevation view of the device with the clasp shown in the open position.
Figure 5:
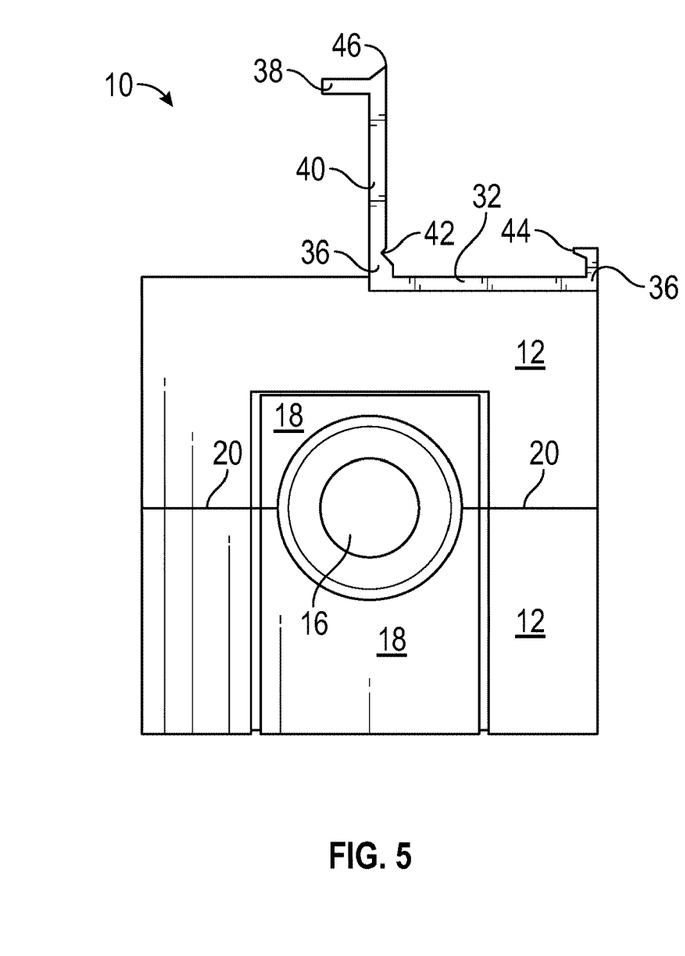
FIG. 5 is a right side elevation view of the device with the clasp shown in the open position.
Figure 6:
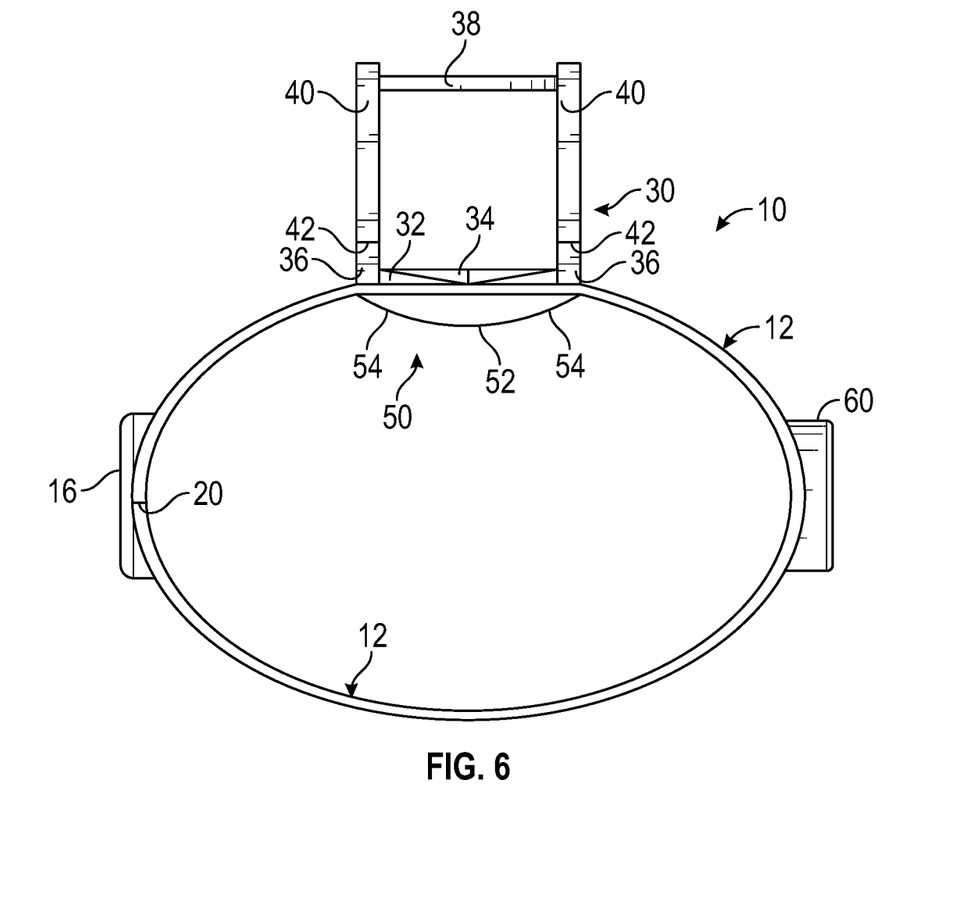
FIG. 6 is a front elevation view of the device with the clasp shown in the open position.

Referring also to FIGS. 2-6, the structure of the sheath support mount 30 is shown in further detail, also showing the mount in both in the open position. Regarding structural details, the mount 30 includes a sheath base 32 that is attached directly to the exterior surface of the wristband 12. The sheath base 32 is shown as having a substantially rectangular shape in which each corner of the base 32 includes a corner post or support 36 that protrudes from the base 32. The base also incorporates a channel or recess 34 which may help to provide additional space for attachment of an introducer sheath. Referring specifically to FIG. 2, the supports 36 located at one end of the base 32 are secured to a pair of corresponding side rails 40 forming part of a clasp that allows a user to selectively mount and remove an introducer sheath. At the connection point between the supports 36 and the side rails 40 are respective notches 42 which create thinned areas creating hinges thus allowing the clasp to be rotated from a closed position as shown in FIG. 1 to an open position shown in FIG. 2. The opposite ends of the rails 40 are connected by a bridge element 38. These ends of the rails may be defined as engaging tips 46 with angled or chamfered edges that selectively engage locking flanges 44 formed on the other two supports 36. The spacing of the engaging tips 46 with respect to the locking flanges 44 may result in an audible "click" sound as the engaging tips 46 contact and are snapped in place with respect to the locking flanges 44. This selective locking feature ensures that the clasp does not inadvertently open without adequate pressure being applied to the bridge to remove the engaging tips from contact with the locking flanges 44.

Located on the interior surface or edge of the wristband 12 is a hemostatic element 50. This element 50 is inflatable to provide a desired amount of pressure against an access point. The element 50 communicates with an inflation port 60 which can be connected to a source of air, such as a syringe (not shown) or some other device that can convey a desired volume of air into the element 50.

The particular shape of the hemostatic element 50 as shown in the figures includes a crown 52 which represents a center area of the element 50 which protrudes the greatest distance from the interior surface of the wristband. The element 50 further includes substantially symmetrical sloping side edges 54 that have curvatures resulting in the element 50 having a partial elliptical shape for the portion of the element 50 exposed in the figures. Although a particular shape and size is illustrated for the element 50, it should be understood that others are contemplated. For example, the exposed portion of the element 50 could have a greater or lesser curvature, or could be substantially flat or planar.

One objective for the hemostatic element 50 is to provide a selectively controlled amount of pressure to be applied to the access area, along with pressure applied to a desired area. Thus, two parameters specifically contemplated in the present invention is the ability to modify the shape and curvature of the element 50, and the overall size of the element 50.

Figure 7:
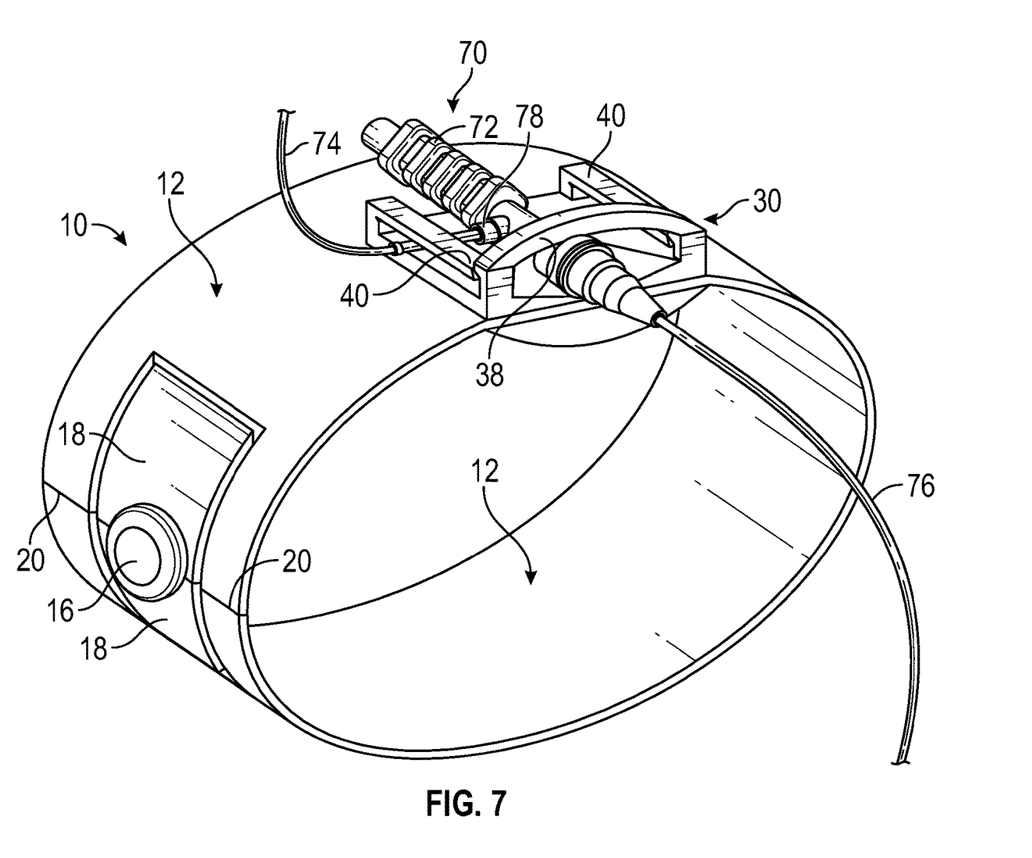
FIG. 7 is another perspective view of the device similar to the perspective view of FIG. 1 in which a medical device is secured by the support mount, namely, an introducer sheath is secured by the support mount shown in the closed or locked position.
Figure 8:
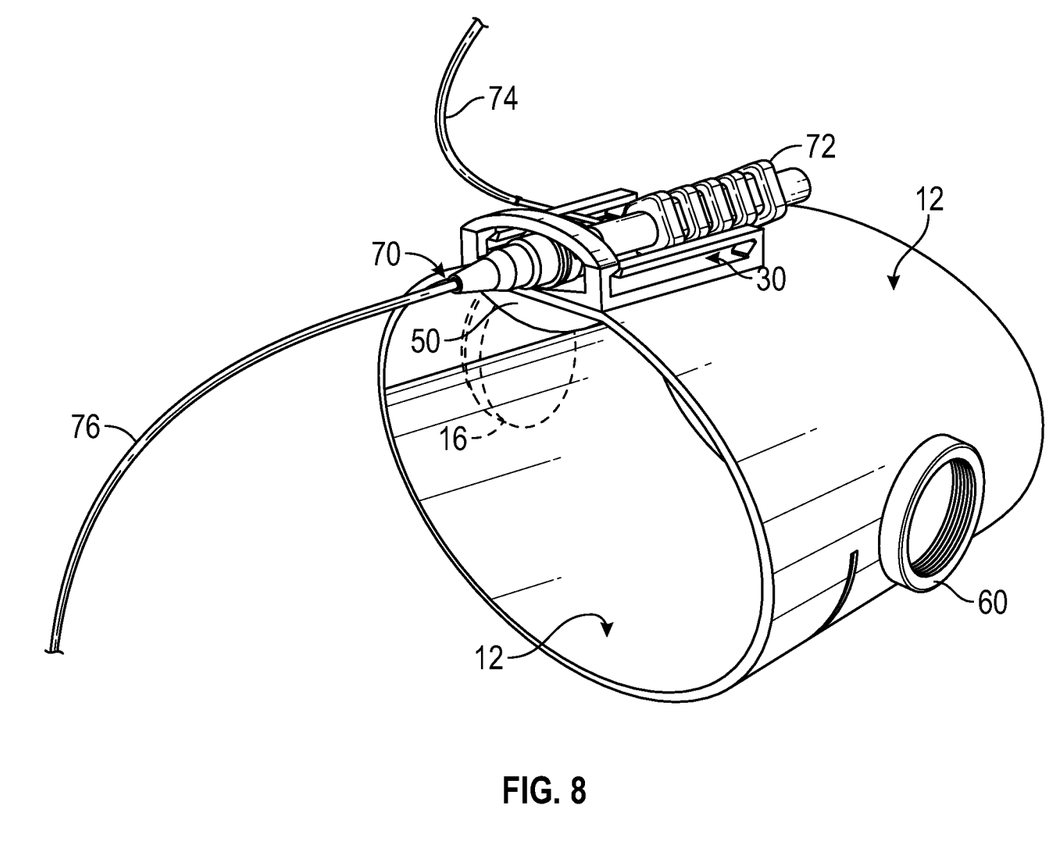
FIG. 8 is another perspective view of the device showing the introducer sheath secured by the support mount.

Referring to FIGS. 7 and 8, an example introducer sheath 70 is shown as secured by the support mount 30 of the invention. As shown, the introducer sheath 70 includes a body 72, an elongated lead 76 forming the introducer sheath catheter or tube that is placed within an artery of a patient, a side port 78, and a side port tube 74. The tube 74 can be used to receive the specific medical device that may be routed through the vascular system of the patient. Such devices may include elongated wires or other similar devices.

The bridge 38 is used to capture a portion of the body 72. The front opening or gap 75 located between the bridge 38 and the forward edge of the base 32 allows the sheath 70 to extend beyond the mount 30. The side port tube 74 extends through the lateral or side opening 77 formed between the lateral edge of the base 32 and the corresponding rail 40.

According to this configuration, the mount 30 is capable of easily accommodating a number of sizes and types of introducer sheaths. Further, the dual side openings 77 allow side ports 74 or any other laterally extending structure of the introducer sheath to be captured which also provides additional support to hold the introducer sheath in place. It should be apparent from the particular configuration of the support mount 30 that it provides a stable yet relatively simple structure that allows a user to easily mount and remove a desired introducer sheath from the wristband.

Figure 9:
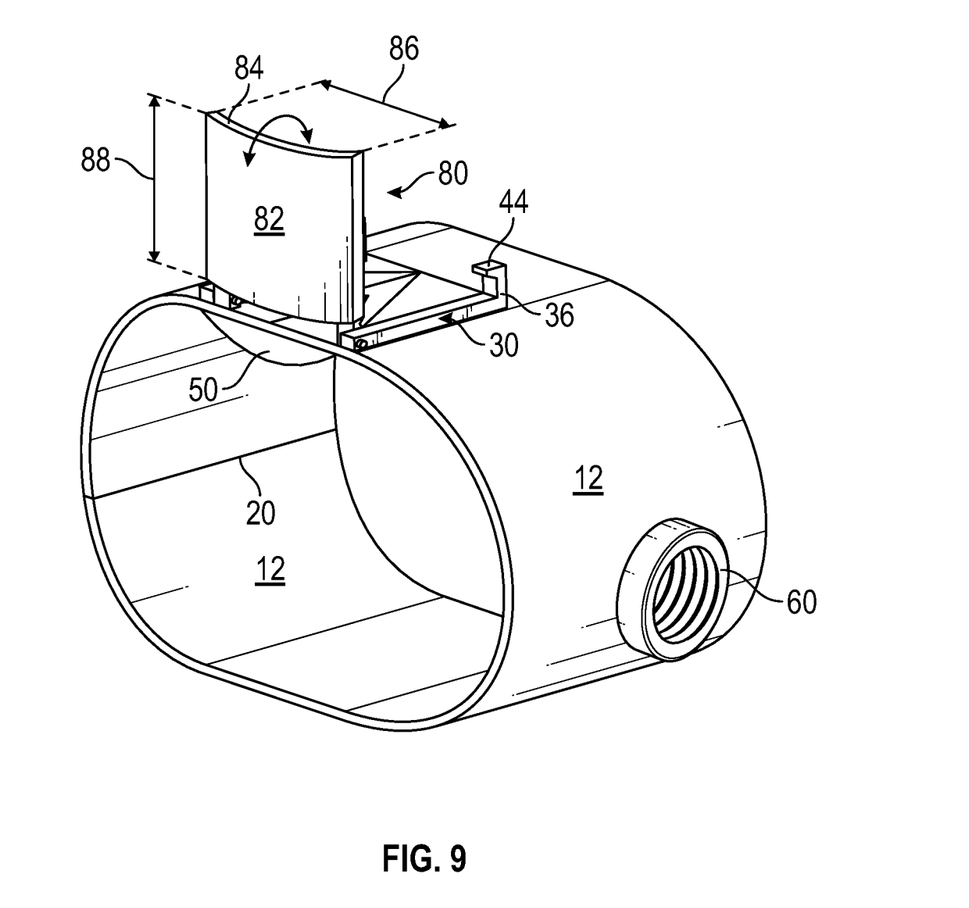
FIG. 9 is a perspective view of another preferred embodiment showing a different configuration for the clasp in which the clasp is rotatable between first and second positions.
Figure 10:
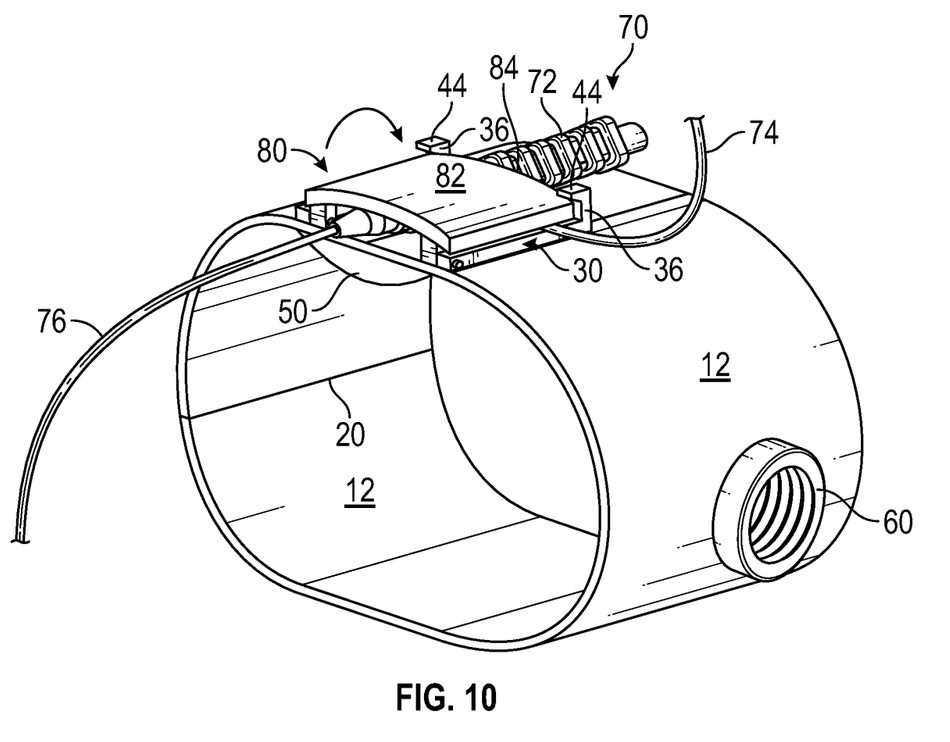
FIG. 10 is a perspective view of the embodiment of FIG. 10 showing the clasp in the first position to lock and hold a surgical instrument or device such as the illustrated transradial introducer sheath.
Figure 11:
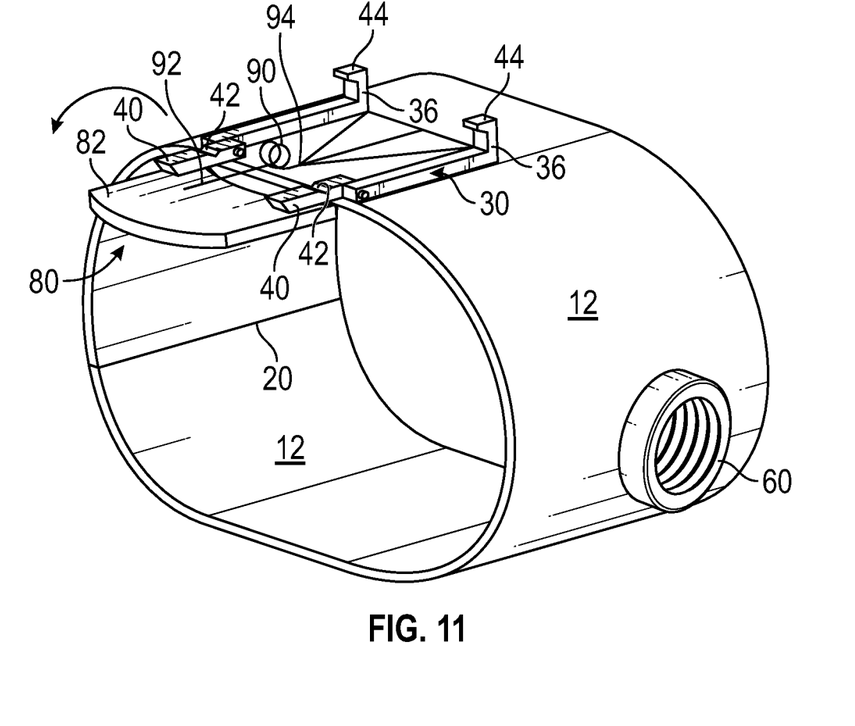
FIG. 11 is another perspective view of the embodiment of FIG. 9 showing the clasp in the second position in which the clasp is rotated to be placed in contact with the patient to act as a hemostasis element.

Referring to FIGS. 9-11, another preferred embodiment is illustrated in which the clasp 80 is provided in a different configuration. The same reference numerals used in these figures correspond to the same structural elements from the prior embodiment. In this particular embodiment, the clasp 80 is a convex shaped element forming a cover 82. The cover is further defined as having a lateral width 86 and a longitudinal length 88. More specifically, when the clasp is rotated as shown in FIG. 11, the clasp 80 is positioned such that the width 86 extends laterally across the patient's wrist or forearm and is generally centered across the width of the wrist or forearm. The length 88 extends longitudinally along the length or long axis of the patient's wrist or forearm.

In a first position shown in FIG. 10, the clasp 80 is rotated to be closed thereby locking the clasp against the base as in the previous embodiments. More specifically, the cover 82 can be selectively locked against the base 30 in which the engaging tips 46 formed at the ends of rails 40 engage the locking flanges 44. When the clasp 80 is moved to the first closed position, the forward or distal edge 84 of the cover is located near a mid-portion of a width of the wristband 12 as shown. The cover 82 provides adequate surface area to engage and hold the introducer sheath 70. The convex or curved shape of the cover 82 also provides for an increased space located between the exterior surface of the wristband 12 and the components of the introducer sheath 70 that are covered by the cover 82.

In a second position shown in FIG. 11, the cover 82 is rotated such that the convex surface faces the patient's forearm or wrist, and the cover is rotated to an extent such that the convex surface makes contact with the patient to provide hemostasis. When the cover 82 is rotated to the second position, the cover can function as a primary hemostasis element or a secondary hemostasis element. As a primary hemostasis element, the cover 82 may be capable of applying sufficient pressure to replace the hemostasis element 50 described in the other elements. As a secondary hemostasis element, the cover 82 may act to supplement pressure to be applied to one or more areas on a patient that may require hemostasis. In most cases, there is a single access point where a medical practitioner makes access through the patient's skin to an artery. Occasionally, there may be multiple access points, and in this case, the hemostasis element 50 could be used to apply pressure to a first access point, and the cover 82 could be used to apply pressure to another access point, or to supplement pressure near the hemostasis element 50.

While the hemostasis element 50 is shown in FIGS. 9-11, if the cover 82 is to be used as a primary hemostasis element, the element 50 is not required and therefore the element 50 should not be considered a mandatory component of the device 10.

FIGS. 9-11 show another optional feature with respect to the cover 82 functioning as a hemostatic element, namely, a pressure adjustable spring 90 that can be used to adjust an amount of pressure the cover 82 places against the patient. The cover is normally urged to the second position with the spring arrangement shown. One leg 92 of the spring is attached to the cover 82 and the other leg 94 is attached to the base 30.

Other types of springs can be used to include additional springs or other configurations of adjustable springs so that a desired amount of pressure is placed by the cover 82 against the patient. In this regard, the spring may also be referred to more broadly as a selectively adjustable pressure component in which a selected setting on the component allows for a desired amount of pressure to be exerted by the cover 82. Therefore, the spring 90 shown is intended to represent but one simplified example of an adjustable pressure component.

Although the cover 82 is shown with a convex surface, it is also contemplated the convex surface can be modified in shape to best produce a pressure supplying force for hemostasis. For example, the cover could have a centrally located protrusion (not shown) capable of providing greater direct pressure at a smaller targeted location on the patient.

According to another aspect of the invention, the wristband 12 may be inflatable. The wristband includes the interior and exterior surfaces, and these surfaces may correspond to separate pieces of material such that a selected gap between the back to back pieces of material may serve as reservoir(s) to receive air. The port 60 may also be used to supply air to the reservoir(s) to selectively inflate the wristband. Alternatively, a separate port (not shown) similar to port 60 may be used as a dedicated inflation port to inflate the wristband. If only one port 60 is used for inflation of both the hemostatic element 50 and the wristband, a small manual valve (not shown) mounted on the exterior of the wristband and downstream of the port 60 can be used to direct air to the element 50 or wristband.

According to a method of the invention, a user selects a wristband from a possible group of wristbands having a desired width and length. The wristband may be made from a flexible piece of material in which the circumference of the wristband is adjustable to specifically fit the patient to which the wristband is applied by a closure device. The wristband may include one or more inflatable areas to assist in keeping the wristband secured to the patient, and may be selectively inflated to provide supplemental pressure to an access point created during a medical procedure. A device such as an introducer sheath is secured to the wristband by opening the clasp, positioning the introducer sheath in contact with a base of the support mount, and then closing the clasp. Laterally extending parts of the introducer sheath may extend through one or both of the side openings of the support mount. A user knows when the clasp is locked in place in the closed position, such as by an audible "click" corresponding to engaging tips that engage corresponding locking flanges of the support mount. During the medical procedure, the wristband remains secured to the patient. After the procedure, the elongate lead of the introducer sheath is removed from the patient. The hemostatic element is preferably placed over the access point during the procedure such that when the elongate lead is removed, a desired amount of pressure may instantaneously be applied to the access point. Additionally, some amount of pressure applied to the access point may occur even prior to removal of the lead of the introducer sheath so that there is no gap between removal of the introducer sheath and application of pressure.

According to another aspect of the invention, a pressure sensing element may be incorporated in the hemostatic element to measure the amount of pressure placed upon the access point of the patient to include pressure applied at any time before, during, and after the medical procedure. The measured pressure may be an input to an electronic controller which may include preprogrammed instructions for applying a known amount of pressure to the access point. The inflation port of the wristband may communicate with a source of pressurized air which is automatically controlled by the electronic controller. In this way, an automated sequence may be provided for manipulating the hemostatic element.

According to yet another aspect of the invention, if the applied pressure is not enough to adequately stop bleeding, the user may manually intervene and increase the amount of pressure as well as the duration of pressure. Further, the user may provide an input to the electronic controller which in turn executes the user instruction by application of the desired amount of pressure and/or duration of the pressure.

Although the invention has been described with respect to one or more preferred embodiments, it shall be understood that the invention is not limited to these specific embodiments and therefore the invention should be understood to cover the claims appended hereto and equivalents thereof.

What is claimed is:

1. A transradial sheath support and hemostasis device comprising:
   a flexible wristband;
   a closure device incorporated on the wristband to selectively size a circumference of the wristband with respect to a patient who receives the wristband;
   a sheath support mounted to the wristband, said sheath support made of a molded thermoplastic material;
   said sheath support comprising a base, a plurality of posts extending from the base, and a clasp rotatably connected to said sheath support, said sheath support being selectively movable between a first position in which the clasp is rotated away from the base, and a closed position in which the clasp is rotated towards the base and secured thereto;
   an inflatable hemostatic element secured to an interior surface of the wristband and aligned with said sheath support, said hemostatic element communicating with a source of air to selectively inflate said hemostatic element; and
   wherein said clasp of said sheath support comprises a pair of spaced rails having first ends connected to corresponding posts of said plurality of posts and second ends connected to a bridge extending transversely between said rails.

2. The transradial sheath support and hemostasis device, as claimed in claim 1, wherein:
   a first opening is formed between said bridge and a front edge of said base.

3. The transradial sheath support and hemostasis device, as claimed in claim 1, wherein:
   a pair of lateral side openings is formed between respective side rails and lateral side edges of said base.

4. The transradial sheath support and hemostasis device, as claimed in claim 1, further including:
   an inflation port communicating with said hemostatic element for introduction of air into said hemostatic element to selectively change pressure said hemostatic element.

5. The transradial sheath support and hemostasis device, as claimed in claim 1, further including:
   a closure stiffener incorporated on said wristband to provide stiffening support to said closure device.

6. The transradial sheath support and hemostasis device, as claimed in claim 1, wherein:

said side rails each further include an engaging tip which is selectively engageable with corresponding locking flanges formed on two posts of said plurality of posts.

7. A transradial sheath support and hemostasis device comprising:
a flexible wristband;
a closure device incorporated on the wristband to selectively size a circumference of the wristband with respect to a patient who receives the wristband;
a sheath support mounted to the wristband, said sheath support made of a molded thermoplastic material;
said sheath support comprising a base, a plurality of posts extending from the base, and a clasp rotatably connected to said sheath support, said sheath support being selectively movable between a first open position in which the clasp is rotated away from the base, and a closed position in which the clasp is rotated towards the base and secured thereto;
means for providing hemostasis to an access point of the patient, said means for providing hemostasis being secured to an interior surface of the wristband and aligned with said sheath support, said means for providing hemostasis communicating with a source of air to selectively inflate said means for providing hemostasis; and
said clasp of said sheath support comprises a pair of spaced rails having first ends connected to corresponding posts of said plurality of posts and second ends connected to a bridge extending transversely between said rails.

8. The transradial sheath support and hemostasis device, as claimed in claim 7, wherein:
a first opening is formed between said bridge and a front edge of said base.

9. The transradial sheath support and hemostasis device, as claimed in claim 7, wherein:
a pair of lateral side openings is formed between respective side rails and lateral side edges of said base.

10. The transradial sheath support and hemostasis device, as claimed in claim 7, further including:
an inflation port communicating with said means for providing hemostasis to introduce air into said means for providing.

11. The transradial sheath support and hemostasis device, as claimed in claim 7, further including:
a closure stiffener incorporated on said wristband to provide stiffening support to said closure device.

12. The transradial sheath support and hemostasis device, as claimed in claim 7, wherein:
said side rails each further include an engaging tip which is selectively engageable with corresponding locking flanges formed on two posts of said plurality of posts.

13. The transradial sheath support and hemostasis device, as claimed in claim 1, further including:
a pressure sensing element communicating with a controller to input information to said controller relating to an amount of applied pressure placed on the patient by said hemostatic element.

14. The transradial sheath support and hemostasis device, as claimed in claim 13, further including:
an output associated with said controller to provide a source of air to said hemostatic element to selectively inflate or deflate said hemostatic element based on pressure sensed by said pressure sensing element.

15. A method of providing transradial sheath support and hemostasis comprising:
providing a flexible wristband, a closure device incorporated on the wristband to selectively size a circumference of the wristband with respect to a patient who receives the wristband, a sheath support mounted to the wristband, said sheath support made of a molded thermoplastic material, said sheath support comprising a base, a plurality of posts extending from the base, and a clasp rotatably connected to said supports, said clasp of said sheath support comprising a pair of spaced rails having first ends connected to corresponding posts of said plurality of posts and second ends connected to a bridge extending transversely between said rails said sheath support being selectively movable between a first open position in which the clasp is rotated away from the base, and a closed position in which the clasp is rotated towards the base and secured thereto;
a. providing an inflatable hemostatic element secured to an interior surface of the wristband and aligned with said sheath support, said hemostatic element communicating with a source of air to selectively inflate said hemostatic element;
placing the wristband on the patient and aligning the hemostatic element over an access point on the patient in which access was made to a vascular system of the patient by an introducer sheath;
mounting the introducer sheath on the sheath support; and
selectively applying pressure to the access point at a selected time during, after, or during and after said introducer sheath is removed from the access point.

16. The method, as claimed in claim 15, wherein:
said pressure is monitored by an electronic controller communicating with a pressure sensing element mounted to said hemostatic element.

17. A transradial sheath support and hemostasis device comprising:
a flexible wristband;
a closure device incorporated on the wristband to selectively size the wristband with respect to a patient who receives the wristband;
a sheath support mounted to the wristband, said sheath support made of a molded thermoplastic material, and a clasp rotatably connected to said sheath support, said clasp including a cover with an upper curved convex surface thereof that creates a gap between a lower surface of said cover and an exterior surface of said wristband, said clasp being selectively movable between a first position in which the clasp is rotated towards and secured to the wristband for securing a device such as a transradial sheath, and a second position in which the clasp is rotated away from the wristband and the upper curved convex surface is positioned against the patient to function as a first hemostatic element by applying pressure to a selected location on the patient.

18. The transradial sheath support and hemostasis device, as claimed in claim 17, wherein:
said sheath support further includes a base, and said clasp being rotatably mounted to said base and said clasp extending beyond said base adjacent a side edge of said wristband.

19. The transradial sheath support and hemostasis device, as claimed in claim 17, further including:
a second hemostatic element secured to an interior surface of the wristband and aligned with said sheath support.

20. The transradial sheath support and hemostasis device, as claimed in claim 17, further including:

a selectively adjustable pressure component communicating with said clasp and secured to said wristband for applying a selected pressure to said clasp for achieving hemostasis.

21. The transradial sheath support and hemostasis device, as claimed in claim 20, wherein:
said selectively adjustable pressure component includes a spring.

22. The transradial sheath support and hemostasis device, as claimed in claim 19, wherein:
said second hemostatic element is inflatable.

23. A method of providing transradial sheath support and hemostasis comprising:
attaching a flexible wristband to a patient;
providing a closure device incorporated on the wristband to selectively size the wristband with respect to the patient;
providing a sheath support mounted to an exterior surface of the wristband and a clasp rotatably connected to said sheath support;
moving said clasp to a first position in which the clasp is rotated towards and secured to the wristband for securing a device such as a transradial sheath; and
moving said clasp to a second position in which the clasp is rotated away from the wristband and positioned against the patient to function as a hemostatic element by applying pressure to a selected location on the patient.

\* \* \* \* \*

UNITED STATES PATENT AND TRADEMARK OFFICE
CERTIFICATE OF CORRECTION

PATENT NO. : 11,134,957 B2
APPLICATION NO. : 15/694525
DATED : October 5, 2021
INVENTOR(S) : Jonathan Cole Harding, Philip Harding and William L. Schaal It is certified that error appears in the above-identified patent and that said Letters Patent is hereby corrected as shown below:

In the Claims

Column 11, Lines 66-67 to Column 12, Lines 1-29, should read:
A method of providing transradial sheath support and hemostasis comprising:
   providing a flexible wristband, a closure device incorporated on the wristband to selectively size a circumference of the wristband with respect to a patient who receives the wristband, a sheath support mounted to the wristband, said sheath support made of a molded thermoplastic material, said sheath support comprising a base, a plurality of posts extending from the base, and a clasp rotatably connected to said supports, said clasp of said sheath support comprising a pair of spaced rails having first ends connected to corresponding posts of said plurality of posts and second ends connected to a bridge extending transversely between said rails said sheath support being selectively movable between a first open position in which the clasp is rotated away from the base, and a closed position in which the clasp is rotated towards the base and secured thereto;
providing an inflatable hemostatic element secured to an interior surface of the wristband and aligned with said sheath support, said hemostatic element communicating with a source of air to selectively inflate said hemostatic element;
   placing the wristband on the patient and aligning the hemostatic element over an access point on the patient in which access was made to a vascular system of the patient by an introducer sheath; mounting the introducer sheath on the sheath support; and
   selectively applying pressure to the access point at a selected time during, after, or during and after said introducer sheath is removed from the access point.

Signed and Sealed this
Fourth Day of January, 2022

Drew Hirshfeld
*Performing the Functions and Duties of the
Under Secretary of Commerce for Intellectual Property and
Director of the United States Patent and Trademark Office*